(12) United States Patent
Cohen et al.

(10) Patent No.: US 6,225,126 B1
(45) Date of Patent: May 1, 2001

(54) METHOD AND APPARATUS FOR MEASURING HEMOSTASIS

(75) Inventors: Eli Cohen, Skokie; Peter R. Delmenico, Evanston; Gabriel Ravin, Glenview, all of IL (US); William R. George, Santa Cruz, CA (US); John A. Lake, Evanston, IL (US)

(73) Assignee: Haemoscope Corporation, Skokie, IL (US)

( * ) Notice: Subject to any disclaimer, the term of this patent is extended or adjusted under 35 U.S.C. 154(b) by 0 days.

(21) Appl. No.: 09/255,099

(22) Filed: Feb. 22, 1999

(51) Int. Cl.⁷ .................................................. G01N 33/86
(52) U.S. Cl. .......................... 436/69; 422/73; 600/368; 600/369; 600/371; 73/64.41; 73/64.42
(58) Field of Search .......................... 436/43, 54, 69; 422/63, 68.1, 73; 600/368, 369, 371; 73/64.41, 64.42

(56) References Cited

U.S. PATENT DOCUMENTS

| | | | |
|---|---|---|---|
| 3,714,815 | * 2/1973 | Hartert | 73/64.41 |
| 4,148,216 | * 4/1979 | Do et al. | 73/54.26 |
| 4,193,293 | 3/1980 | Cavallari | 73/54.41 |
| 4,312,217 | * 1/1982 | Hartert | 73/64.42 |
| 4,317,363 | * 3/1982 | Shen | 73/64.41 |
| 4,328,701 | * 5/1982 | Mau-Tung et al. | 73/54.26 |
| 4,695,956 | * 9/1987 | LeVeen et al. | 435/13 |
| 5,223,227 | * 6/1993 | Zuckerman | 422/102 |
| 5,523,238 | * 6/1996 | Varon et al. | 436/69 |
| 5,777,215 | * 7/1998 | Calatzis et al. | 73/64.41 |
| 5,854,423 | 12/1998 | Venegas | 73/64.41 |

FOREIGN PATENT DOCUMENTS

| | | |
|---|---|---|
| 37 38 901 A1 | 5/1989 | (DE) . |
| 0 018 905 A1 | 11/1980 | (EP) . |
| 0 404 456 A2 | 12/1990 | (EP) . |
| 2 389 137 | 11/1978 | (FR) . |
| 2 004 376 | 3/1979 | (GB) . |

OTHER PUBLICATIONS

CSA● Clot Signature Analyzer—Global Screening Device for Hemostasis, Xylum Corporation (4 pages), date unknown.

Orbitometer—The consequent development of the precursory Thrombo–Elastography (Hartert 1947) and of Resonance–Thrombography (Hartert 1977), Heinrich Amelung GmbH (6 pages), date unknown.

roTEG Coagulation Analyzer, 1997 Dynabyte Medical (2 pages).

roTEG Coagulation Analyzer—whole blood coagulation analysis (4 pages), 1996.

elvi 816—Dual Channel, B1 Clot Thromboelastograph, Logos Scientific Inc. (2 pages) date unknown.

TE–700—New Type Clot–Tracer Model TE–700, Erima (4 pages in Japanese), with translation (2 pages in English), date unknown.

International Search Report for International Application No. PCT/US00/04538 dated Jun. 26, 2000.

* cited by examiner

Primary Examiner—Maureen M. Wallenhorst
(74) Attorney, Agent, or Firm—Marshall, O'Toole, Gerstein, Murray & Borun

(57) ABSTRACT

A method and apparatus are provided for measuring hemostasis. The apparatus includes a torque sensing column having a torque sensing element and a drive ring disposed around a body of the column and in registration with the column so as to allow rotation of the drive ring around a longitudinal axis of the column. The apparatus further includes a first guide shaft rigidly secured to the drive ring, the guide shaft extending parallel to the longitudinal axis of the column and a cup holder movably attached to the guide shaft, allowing the cup holder to move parallel to the longitudinal axis of the column. The apparatus also includes a sample cup adapted to engage the cup holder on a outer surface and the torque sensing element of the torque sensing column on an inner surface.

34 Claims, 3 Drawing Sheets

METHOD AND APPARATUS FOR MEASURING HEMOSTASIS

FIELD OF THE INVENTION

The field of the invention relates to testing of blood samples and more particularly to devices for testing hemostasis.

BACKGROUND OF THE INVENTION

Methods of measuring the coagulation characteristics of blood are known. Some such devices attempt to simulate the natural flow of blood in the veins and arteries of a living subject.

An accurate measurement of the ability of a patient's blood to coagulate in a timely and effective fashion is crucial to certain surgical and medical procedures. Accelerated (rapid) and accurate detection of abnormal coagulations is also of particular importance with respect to appropriate treatment to be given to patients suffering from clotting disorders. Often the condition of such patients makes it necessary to administer anti-coagulants, certain fibrinolytic agents, anti-platelet agents, or blood components in a quantity which may only be determined after taking into account the abnormal components or "factors" of the patient's blood which may be contributing to the clotting disorder.

One measure of blood clotting is provided by the Thromelastograph (TEG®) Coagulation Analyzer manufactured by Haemoscope of Skokie, Ill. The Haemoscope device measures the mechanical properties of the clot throughout its structural development.

A number of references describe instruments for measuring blood clotting characteristics based upon simple mechanical movements. These instruments monitor the elastic properties of blood as it is induced to clot under a low shear environment resembling sluggish venous blood flow. The patterns of change in shear elasticity enable the determination of the kinetics of clot formation, as well as the strength and stability of the formed clot. The strength and stability of the clot provide information about the ability of the clot to perform the "work of hemostasis" (i.e., stop or prevent abnormal bleeding) and about the adequacy of blood platelet-fibrin interaction. The kinetics of clot formation provide information about coagulation factors available for clot formation. Analysis of the information provides results which are useful to predict bleeding, to monitor and manage thrombosis, and to monitor fibrinolysis.

While the instrument of the reference is effective in measuring hemostasis based upon resistance to mechanical movement, the apparatus necessary to cause movement and torque measurement is unnecessarily complex. The apparatus is even more difficult to load and unload. Because of the importance of measuring blood clotting, a better apparatus for measuring hemostasis is needed.

SUMMARY

A method and apparatus are provided for measuring hemostasis. In one embodiment, the apparatus includes a torque sensing column having a torque sensing element and a drive ring disposed around a body of the column and in registration with the column so as to allow rotation of the drive ring around a longitudinal axis of the column. The embodiment further includes a first guide shaft rigidly secured to the drive ring, the guide shaft extending parallel to the longitudinal axis of the column and a cup holder movably attached to the guide shaft, allowing the cup holder to move parallel to the longitudinal axis of the column. The embodiment also includes a sample cup assembly adapted to engage the cup holder on an outer surface and the torque sensing element of the torque sensing column on an inner surface.

The apparatus includes novel features which allow for the quick and easy replacement of blood samples. A unobstructed front surface of the apparatus allows the operator better access for easier cup and blood sample placement. A control lever on a torque measuring column of the apparatus allows a pin of the sample cup assembly to be quickly and easily ejected. The sample cup holder may be lifted to a convenient position and a button on the bottom of the holder activated to release the sample cup assembly for easy removal.

DETAILED DESCRIPTION

Figure 1:
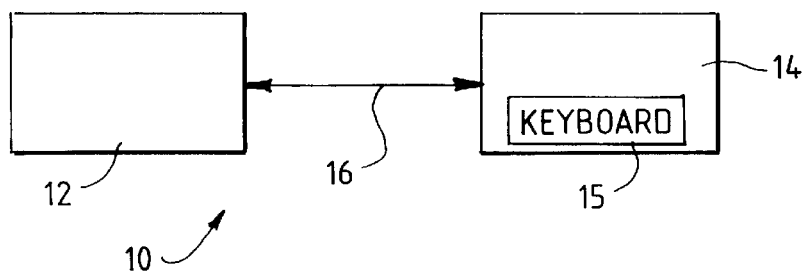
FIG. 1 depicts an embodiment of a system for measuring hemostasis in accordance with the invention.

FIG. 1 is a block diagram of a system 10 for measuring hemostasis, generally, in accordance with an illustrated embodiment of the invention. Included within the system 10 is a measuring unit 12 and data collection unit 14 (e.g., a personal computer (PC), datalogger, etc.). The system 10 is constructed in a modular form. Features discussed below provide for the quick and easy replacement of individual modules of the system 10 without the need for re-calibration or complex re-alignment steps.

Under the illustrated embodiment, hemostasis may be measured by the system 10 in terms of a series of shear elasticity measurements (e.g., in terms of $dyn/cm^2$). The resulting hemostasis profile may be used as a measure of the time it takes for the first fibrin strand to be formed, the kinetics of clot formation, the strength of the clot (in shear elasticity units of $dyn/cm^2$) and dissolution of the clot.

In general, the system 10 measures a clot's physical properties by the use of a combination cylindrical cup and matching shear-inducing pin. The combination cup and matching pin may be constructed generally as taught by U.S. Pat. No. 5,223,227 to Zuckerman, assigned to the assignee of the present invention and incorporated herein by reference.

Figure 2:
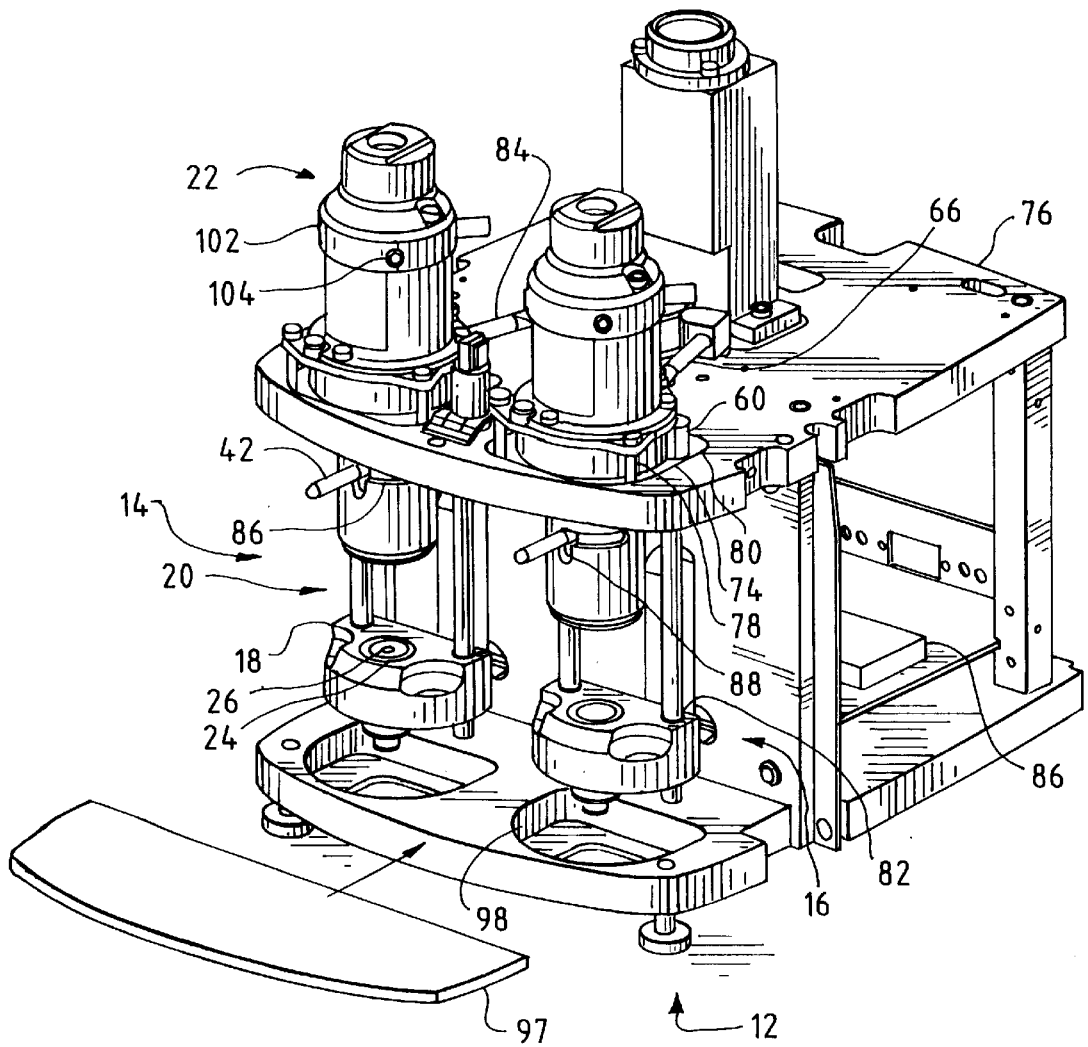
FIG. 2 depicts an embodiment of a measuring unit for use with the system of FIG. 1.

FIG. 2 is a perspective view of one example of the measuring unit 12. Included within the measuring unit 12 may be a first and a second measuring station 14, 16. While the system 10 shows two stations, 14, 16, it should be understood that there is no practical limit of the number of test stations that may be incorporated into the system 10. The measuring stations 14, 16 may be functionally identical and facilitate the processing of two separate blood samples at the same time.

An explanation will now be provided of the operation of the first measuring station 14. For purposes of explanation, it may be assumed that the structure of the second station 16 is substantially identical to first station 14.

Each measuring station 14, 16 may include at least three main structures. The stations 14, 16 may include a cup carrier 18, a cup carrier drive system 20 and a torque measuring column 22.

The cup carrier 18 may be provided with a receptacle sized to accept a sample cup 24 (containing a blood sample). Once a sample cup 24 is inserted into the cup carrier 18, a pin 26 may be inserted into the cup 24 of the cup carrier 18. The sample cup 24 and pin 26 may be fabricated of an inexpensive material (e.g., plastic) intended for a one-time use.

Figure 9:
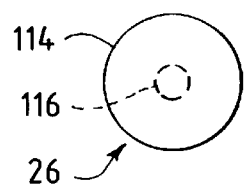
FIG. 9 depicts a top view of a torque measuring pin of the system of FIG. 1.

One difference between the cup and matching pin of the Zuckerman '227 patent over that used herein relates to a configuration of the pin. Under the embodiment, the torque sensing pin 26 (FIG. 9) is provided with a fully enclosing upper flange 114 which functions to completely close an upper opening of the sample cup 24. Such closure has been found important in preserving the integrity of the blood sample against the effects of drying and oxidation.

The pin 26 is also provided with a circular aperture 116. The circular aperture reduces the difficulty in engaging the pin 26 with the torque measuring column 22 as explained in more detail below.

Once the sample cup 24 and pin 26 is inserted into the cup carrier 18, the carrier 18 may be manually lifted into contact with a bottom of the torque measuring column 22. Once the carrier 18 makes contact with the bottom of the measuring column 22, a skewer 28 (see cross-sectional view of the column 22 in FIG. 3) engages the circular center hole of the pin 26.

Figure 4:
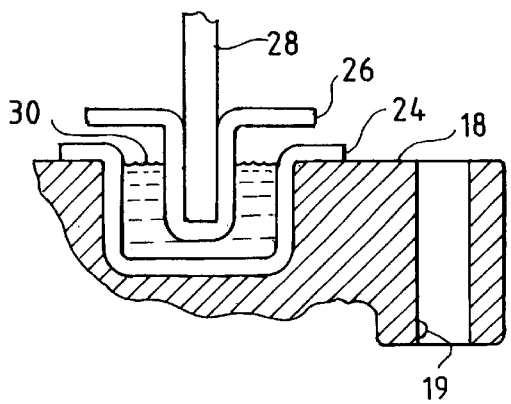
FIG. 4 depicts an example of a sample cup carrier for use with the measuring unit of FIG. 2.

FIG. 4 is a cut-away view of an embodiment of the cup carrier 18. Shown included within the cup carrier 18 is a sample cup 24 and pin 26. Shown between the cup 24 and pin 26 is a blood sample 30.

The cup 24 may be fabricated for any convenient size blood sample (e.g., 360 $\mu$L) consistent with sampling accuracy. An outer diameter of the pin 26 and inner diameter of the cup 24 may be selected to provide a 1 mm gap on each side (2 mm total) within which the blood sample resides.

During testing, the cup holder 18 is oscillated 30 (i.e., rotated) around the longitudinal axis of the skewer 28. For example, the cup holder 18 may be rotated to a distance of 2.4 degrees on either side of a center point during each cycle (4.83 degrees of total travel). Each cycle may last 10 seconds with a 1½ second rest period at each end of the excursion.

During rotation of the cup holder 18 and cup 24, the relative movement of the cup 24 and stationary position of the pin 26 creates a shear action between the inner surface of the cup 24 and outer surface of the pin 26. The shearing action causes a shear movement among adjacent blood molecules lying between, resulting in coagulation.

As the blood coagulates, the shear resistance between adjacent molecules in the blood sample increases and the shear force that may be transmitted from the cup 24 to the pin 26 increases. By measuring the torque imparted to the skewer 28 through the blood 30, a thrombo-elastic graph may be created over a time period.

In order to preserve the integrity of the blood testing process, a port 93 (FIG. 3) is provided through the torque measuring column 22 for introducing a protective oil over the blood sample 30. The port 93 is angled for the insertion of a pipette into the junction area between the pin 26 and cup 24.

By introducing the oil into the area of the junction, capillary action causes the oil to be drawn into the cup 24 and overlay and protect the blood 30. Protection of the blood 30 has been found to be an important feature (against drying of the blood) where extended periods are required for coagulation testing.

As a further feature for protection of the blood sample 30, a relatively closed cavity 38 is provided at the lower end of each torque measuring column 22. The closed cavity functions to provide a protected environment for the blood sample during testing. Such closed cavity 38 not only reduces the possibility that airborne contaminants may enter the sample 30, but also tends to control humidity of the environment surrounding the cup 24.

Figure 3:
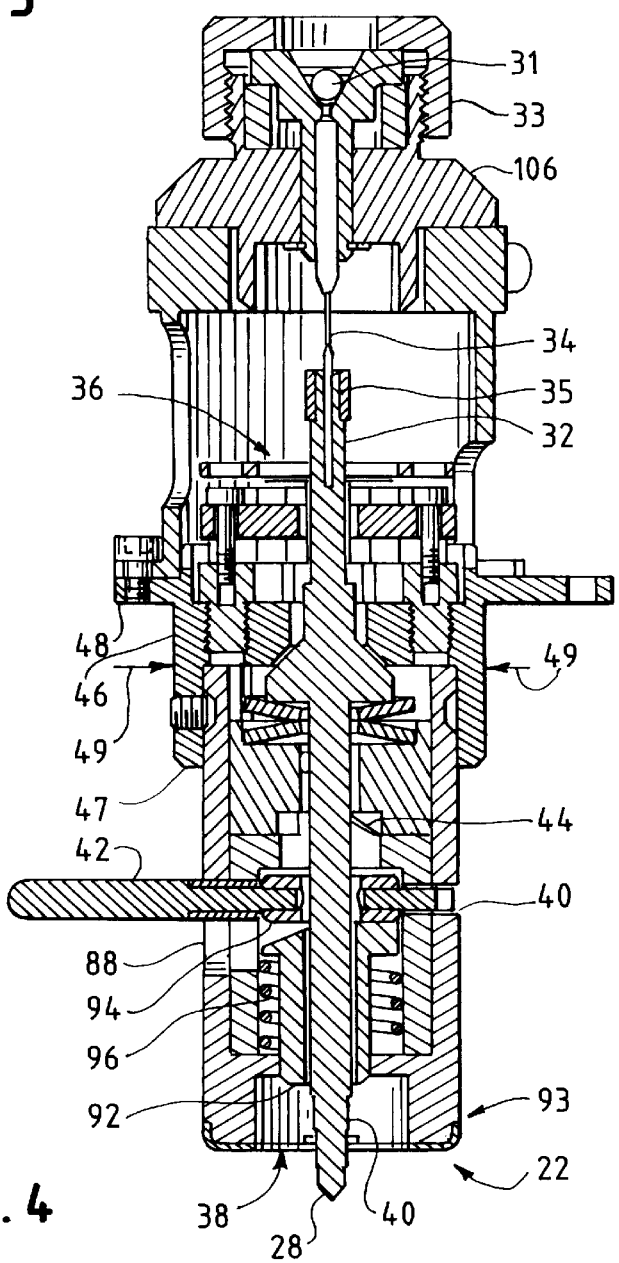
FIG. 3 depicts an embodiment of a torque measuring column for use with the measuring unit of FIG. 2.

Returning now to the illustrative example of FIG. 3, it may be seen that the skewer 28 is coupled to a torque transmission shaft 32 which freely floats within the column 22 during test conditions, suspended from a tungsten wire 34. The tungsten wire 34 provides a progressive resistance to torque from the skewer 28.

The tungsten wire, in turn, is supported by a stationary cross-bar 31 disposed in a V-groove. The V-groove provides a vertical reference point for alignment of the pin 26 and cup 24.

An appropriate non-contacting rotation detector (e.g., rotary variable differential transformer (RVTD), rotary variable inductive transformer (RVIT), laser/mirror/CCD arrangement, etc.) 36 may be provided to detect rotation of the transmission shaft 32 (and skewer 28) caused by torque transmitted by the shear force through the blood to the pin 26. By multiplying a detected rotation of the shaft by a spring constant of the tungsten wire 34, a torque value may be periodically determined and transmitted to the data collection unit 14 through the interconnecting cable 16.

The tungsten wire 34 may be fabricated to any appropriate diameter (e.g., 0.007 inch) and length (e.g., 2 inches) consistent with an expected torque measuring range. Further, the column 22 is fabricated for easy replacement of the wire 34 (or the column 22 itself) where it becomes necessary (for research or other purposes) to adjust a torque measuring range. This also greatly simplifies replacement of torsion wires damaged by misuse or otherwise.

The simplified procedure for replacing the torsion wire greatly increases the flexibility and utility of the system 10. For example, the easily replaceable torsion wire allows a weaker torsion wire (for increased sensitivity) to be used for measuring weaker clots, or a stronger torsion wire for stronger clots.

To replace a wire 34, the user moves the control lever 42 to a locked position. Next, the set screw 35 (FIG. 3) is loosened to release the wire 34.

To remove the wire 34, a screw-on cap 33 is removed and a pair of needle-nose pliers (not shown) may be used to grasp an end 31 of the wire 34 and lift it out of the column 22. A replacement wire 34 may be inserted in place of the removed wire 34.

Once the replacement wire 34 is inserted, the set screw 35 may again be tightened. Once the set screw is tightened, the skewer 28 may be centered using centering screws 102, 104

(FIG. 1). Adjustment of the centering screws 102, 104 allows a support cap 106 (FIG. 3) to be laterally adjusted to center the skewer 28 over the cup 24.

Figure 8:
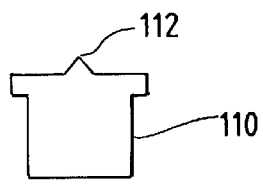
FIG. 8 depicts an alignment fixture that may be used with the system of FIG. 1.

To center the skewer 28 a fixture 110 (FIG. 8) may be inserted in place of the cup 24 into the cup holder 18. A spacer block (not shown) may be used to bring the skewer 28 into vertical proximity with a reference point 112 of the fixture 110. The centering screws 102, 104 may be adjusted as necessary to center the skewer 28 over the reference point 112 of the fixture 110.

To complete installation of the new wire 34, a torque constant (i.e., measured in torque units per degree of deflection) may be entered through the keyboard 15 into the CPU 14. Alternatively, a lookup table of torque constants may be provided within the CPU 14 and accessed via a part number of a wire 34 entered through the keyboard. The torque value may be used to determine a measured torque by multiplying a torque deflection (in degrees) by the torque constant.

Figure 5:
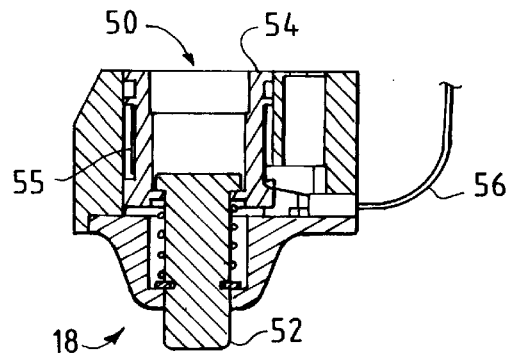
FIG. 5 depicts a cut-away side view of the cup carrier of FIG. 4.

Turning now to loading of the cup carrier 18, a side cut-away view is shown in FIG. 5 of the cup carrier 18. A cavity 50 is provided in an upper surface of the cup carrier 18 to receive the sample cup 24. Once the cup 24 and tip 26 are placed in the cavity 50, the cup carrier is lifted into contact with the bottom of the column 22 of FIG. 3. Once in contact a spring-loaded button 52 provided on the bottom of the cup carrier 18 is activated to seat the tip 26 onto the skewer 28. As the button 52 is activated, an inner hole of the tip 26 is urged onto the skewer 28 up over a shoulder 40 on the skewer 28 within a cavity 38 located in the bottom of the column 22.

Once the tip 26 is seated on the skewer 28, the cup carrier 18 may be lowered and the cup 24 seated back into its own respective cavity 50. After the cup 24 is seated, the cup 24 may be filled with a blood sample 30 and again raised into an operating position against the bottom of the column 22. The cup 24 may be raised and lowered slightly several times, thereby using the pin 26 to mix the sample prior to testing.

Once the carrier 18 has been seated against the column 22, a registration lever 42 (FIG. 2) may be rotated to the right along a slot 86 to a test position. Moving the lever 42 to a test position brings the tip 26 into a proper position with respect to the cup 24. Rotating the lever 42 to the right rotates a cam 44 which lowers the torque transmission shaft 32 from a locked position by a sufficient distance (e.g., 0.035 inch) to bring the tip 26 and cup into a proper spatial alignment with the cup 24.

Once the cup 24 and tip 26 are brought into a proper relationship, an operator (not shown) may enter a patient name through a keyboard 15 on the data recorder 14. At the same time the drive mechanism 20 may be activated and testing may begin.

Figure 6:
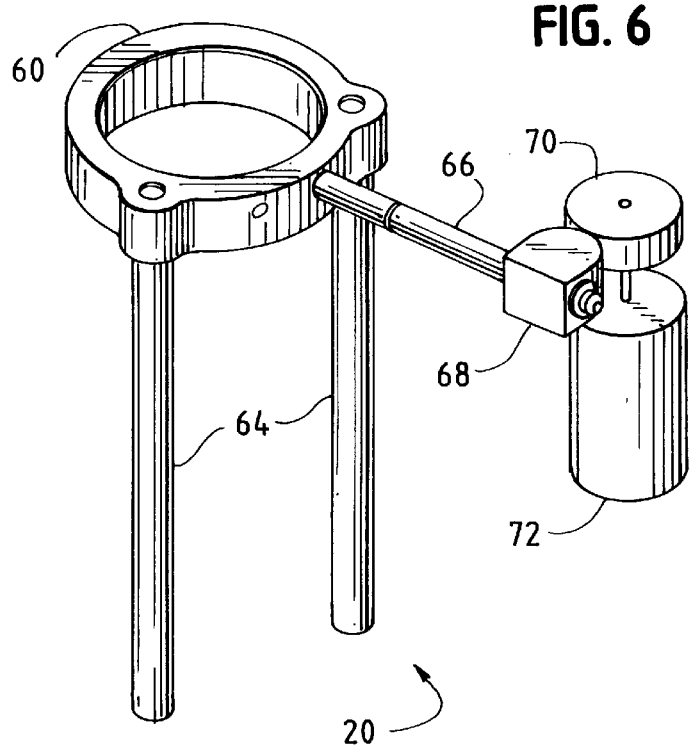
FIG. 6 depicts an example of a drive mechanism of the measuring unit of FIG. 2.

A detached partial perspective view of an illustrative embodiment of the drive system 20 is shown in FIG. 6. While the partial view of FIG. 6 shows the drive system 20 for the right testing station 16, it may be assumed that the drive system for the left testing station 14 would be substantially identical (with the exception of the cam follower 68 facing the other direction).

Included within the drive system is a drive ring 60. A pair of parallel guide shafts 62, 64 extend downwardly from the drive ring 60. A positioning rod 66 extends radially outwardly from the drive ring 60 and engages a geared drive motor 72 through a cam follower 68 and cam 70.

The drive ring 60 circumferentially engages the column 22 around a first abutting surface 46 (FIG. 3). The column 22 maintains the drive ring 60 in a radial alignment with the column 22 by moveable registration of an inner surface of the drive ring 60 against the first abutting surface 46.

Figure 7:
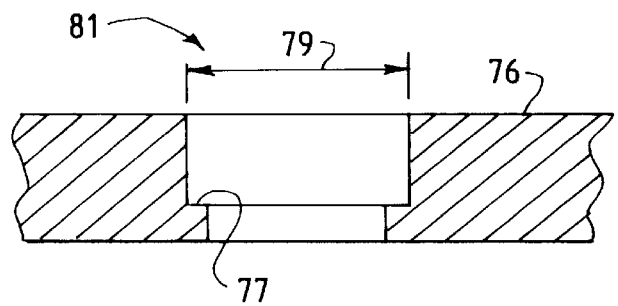
FIG. 7 depicts a side view of a mounting feature of a torque measuring column of the system of FIG. 1.

Longitudinal alignment of the drive ring 60 with the column 22 is maintained by trapping the drive ring 60 between a second abutting surface 48 (FIG. 3) and a mating surface 74 on a top plate 76 of the measuring unit 12. The column 22 is retained in a fixed relationship with the top plate 76 through the use of a stepped hole 81 (FIG. 7). An outer diameter 49 (FIG. 3) of the column 22 is sized to engage the hole 81 of a slightly larger diameter 79 (e.g., 0.005–0.010 inch). A step 77 at the bottom of the hole 81 allows for a fixed spacing between the second abutting surface 48 and top plate 76 and free rotation of the drive ring 60.

A set of three screws 78 may be used to secure the column 22 to the top plate 76. Removal of the screws 78 also allows for the simple replacement of the torque measuring column 22 should the need arise.

The set of guide shafts 62, 64 extend downwardly from the guide ring 60 through a set of slots 80 in the top plate 76 to engage the cup carrier 18. A set of linear bearings 82 on each carrier 18 allow the carrier 18 to be easily moved up or down the guide shafts 62, 64. A set of spring loaded clips 19 (FIG. 4) are provided below each linear bearing 82 to maintain the carrier 19 in a selected position during testing and otherwise.

Movement of the guide ring 60 is accomplished by operation of the positioning rod 66. The cam follower 68 of the positioning rod 66 is maintained in contact with the cam 70 by operation of a spring 84. More specifically, a clockwise motion of the ring 60 (when viewed from above) is caused by the cam. A counterclockwise motion of the ring 60 is caused by the spring 84.

To obtain an appropriate cycling rate, the motor 72 may be geared to obtain a speed of one revolution every 10 seconds. A flat spot may be provided on the cam 70 at a high point and low point to allow for a one and one-half second pause at the end of each direction of travel. The profile of the cam 70 may be changed as needed to provide a wide range of periodic motions.

The CPU 14 may provide for any number of test intervals. For example, a standard test interval of 10–15 minutes may be used. Alternatively, the test may be extended to 2–3 hours for research purposes.

To maintain the blood sample 30 at an optimal temperature (e.g., 98.6° F.+/−0.1° F.) for testing, a heater 54 and temperature sensor 55 (e.g., RTD, thermocouple, etc.) (FIG. 5) are provided within each carrier 18. The temperature sensors 55 are disposed directly against the receptacle holding the cup 24. A flexible cable 56 may be used to connect and control the heater 54 through operation of a temperature controller 86 located within the sampling unit 12.

A dual channel temperature controller (e.g., a Love Controls Model 32A022-9502) may be used to provide separate temperature control and set points for each carrier 18. The use of separate temperature sensors 55 and close proximity to the blood sample 30 ensures that each blood sample 30 is maintained at a precisely controlled temperature. The availability of separate set points on the controller 86 for each carrier provides the versatility of performing standard testing or testing under abnormal conditions.

Once a cup 24 and pin 26 have been installed into the system 10 (as described above), a blood sample 30 may be directed into the cup 24 using a pipette (not shown). The cup 24 may be raised and lowered against the pin 26 to mix the blood. The hemostasis profile may be obtained as described above.

Once testing is complete, the sample cup assembly 24, 26 may be easily removed by a series of quickly executed steps. The tip 26 may be ejected from the skewer 28 by moving the lever 42 to a load position (as shown in FIG. 2). The lever 42 may then be simply moved downward into a second slot 88 to eject the tip 26. Moving the lever 42 downward causes a center ring 94 to move downward based upon its distance from a pivot point 91. As the center ring 94 moves down it presses against a collar 92, which acts against a spring 96 to eject the tip 26.

Once the tip 26 has been ejected, the carrier 18 may be moved to a lower position and the cup 24 and tip 26 removed. The cup 24 and tip 26 may be ejected from the carrier 18 by lowering the carrier 18 until the button 52 on the bottom of the carrier 18 makes contact with a lower cover 97.

With a first hand, an operator may eject the pin 26. At the same time, the operator may begin moving the cup carrier 18 downward with her other hand. As the carrier 18 is moved downward, the cover 97 activates the button 52, lifting the cup assembly. As the button 52 is activated, the operator may remove the cup assembly and replace it with another cup assembly. The sequence of steps may be performed as part of a single rapid sequence of steps without fear of spilling or compromising the integrity of the testing procedure.

Once the cup 24 and tip 26 have been removed, the carrier 18 may also be removed for cleaning and sterilization. To accomplish removal, the cover 97 is first removed. Under the cover 97, a cavity 98 is provided below the ends of the guide shafts 62, 64. The cavities 98 allow the carrier 18 to be easily slid off the ends of the guide shafts 62, 64. Once detached from the guide shafts 62, 64, the carrier 18 may be slid forward and out of the measuring unit 12.

The simple and rugged construction of the test unit 12 allows for reliable and accurate testing of blood samples. The easy removal and disposal of sample cups and tips reduces the possibility of contamination or infection by users. The easy removal and cleaning of related parts further improves upon the overall ease of use of the measuring unit.

Specific embodiments of a method and apparatus for measuring hemostasis according to the present invention have been described for the purpose of illustrating the manner in which the invention is made and used. It should be understood that the implementation of other variations and modifications of the invention and its various aspects will be apparent to one skilled in the art, and that the invention is not limited by the specific embodiments described. Therefore, it is contemplated to cover the present invention and any and all modifications, variations, or equivalents that fall within the true spirit and scope of the basic underlying principles disclosed and claimed herein.

What is claimed is:

1. Apparatus for measuring hemostasis comprising:
   (a) sample retention apparatus comprising:
      a sample cup; and
      a sample tip received within the sample cup and defining a sample space between an inner wall of the sample cup and an outer surface of the sample tip;
   (b) sample articulation apparatus comprising:
      a drive motor having an output shaft;
      a cam coupled to the output shaft for rotation therewith in response to operation of the drive motor;
      a cam follower engaging the cam, the cam follower articulated in response to rotation of the cam;
      a drive ring coupled to the cam follower and articulated therewith; and
      at least one guide shaft extending from the drive ring;
   (c) a sample carrier secured to and axially moveable along said guide shaft between a sample ready position, a sample test position and a sample ejection position, the sample carrier including a cavity within which the sample cup is received and a sample cup ejection mechanism disposed within the cavity; and
   (d) a measuring apparatus including a sensing column;
      wherein, (i) with the sample carrier at the sample ready position the sample retention apparatus is positioned to the sample carrier with the sample cup being disposed within the cavity, (ii) with the sample carrier at the sample test position the sample tip is engaged with the sensing column and the sample cup is articulated with the sample carrier, and (iii) with the sample carrier in the sample ejection position, the sample cup ejection mechanism is engaged with the sample cup and the sample retention apparatus is displaced from the cavity.

2. The apparatus of claim 1, wherein the measuring apparatus further comprises a sample tip ejection mechanism comprising an annular collar disposed around the sensing column, the annular collar coupled to a lever, and the lever being biased in a first position by a spring and moveable to a second position wherein the annular collar engages the sample tip for displacing the sample tip, after being engaged with the sensing column, from the sensing column.

3. The apparatus of claim 1, wherein the sample tip comprises a radially outwardly extending flange, the flange extending over and covering the sample cup.

4. The apparatus of claim 3, wherein, with the sample carrier in the sample test position, the sample cup is engaged with the flange and the sample tip is caused to be engaged with the sensing column.

5. The apparatus of claim 3, wherein the sample cup ejection mechanism comprises:
   a button having a first surface and a second surface, the button disposed within a lower portion of the cavity and axially movable within the cavity;
   a spring disposed between the button and the sample carrier to bias the button in a first position with the sample carrier in the sample ready and the sample test positions; and
   with the sample carrier in the sample ejection position, the button is in a second position wherein the first surface is engaged with a plate secured to a lower portion of the apparatus and the second surface is engaged with the sample cup.

6. The apparatus of claim 5, wherein with the sample carrier in the sample test position, the button is manually actuatable, whereby the second surface is engaged with the sample cup, the sample cup is engaged with the flange and the sample tip is caused to engage the sensing column.

7. The apparatus of claim 3, further comprising a passage formed between the flange and the sample cup, the passage sized to draw a sample protecting fluid by capillary action into the sample cup.

8. The apparatus of claim 1, wherein the measuring apparatus further comprises an annular flange, the sample carrier comprises a planar surface, and
   with the sample carrier in the sample test position, the annular flange and the planar surface form a chamber around the sample retention apparatus.

9. The apparatus of claim 8, wherein the annular flange comprises a port, the port in communication with the sample cup, the port sized to permit the introduction via a pipette of a sample protecting fluid into the sample cup.

10. Apparatus for measuring hemostasis comprising:
   (a) sample retention apparatus comprising:
      a sample cup; and
      a sample tip received within the sample cup and defining a sample space between an inner wall of the sample cup and an outer surface of the sample tip;
   (b) sample articulation apparatus comprising:
      a drive motor having an output shaft;
      a cam coupled to the output shaft for rotation therewith in response to operation of the drive motor;
      a cam follower engaging the cam, the cam follower articulated in response to rotation of the cam;
      a drive ring coupled to the cam follower and articulated therewith; and
      at least one guide shaft extending from the drive ring;
   (c) a sample carrier secured to and axially moveable along said guide shaft between a sample ready position, a sample test position and a sample ejection position, the sample carrier including a cavity within which the sample cup is received; and
   (d) measuring apparatus comprising:
      a non-contacting rotation detector,
      a torsion spring suspended from an upper portion of the measuring apparatus,
      a sensing column suspended from the torsion spring, the sensing column comprising a sensor portion disposed adjacent the non-contacting rotation detector, a sample tip retainer portion at a lower end onto which the sample tip is received and a lock flange, and
      a sensing column lock secured within the measuring apparatus, the sensing column lock including a lever moveable between a first position and a second position, a lock cam engaged with the lever and a release block engaged with the lock cam, wherein with the lever in the first position the release block is engaged with the lock flange and with the lever in the second position the release block is released from the lock flange.

11. The apparatus of claim 10, wherein the sensing column is releasably suspended from the torsion spring and wherein the measuring apparatus comprises an access aperture through which, with the lever in the first position and the sensing column released from the torsion spring, the torsion spring may be one of withdrawn and inserted.

12. The apparatus of claim 10, wherein the torsion spring comprises a portion of wire.

13. The apparatus of claim 10, wherein the torsion spring comprises a spring assembly, the spring assembly having a support member and a spring member extending from the support member, the spring member having a predetermined spring constant.

14. The apparatus of claim 13, wherein the spring member comprises a wire, the wire having one of a first diameter and a second diameter.

15. The apparatus of claim 10, wherein the sample tip retainer portion comprises a tapered cylinder including a pilot portion, and
   the sample tip comprises an aperture sized to engage the tapered cylinder.

16. The apparatus of claim 15, wherein the sensing column lock further comprises a sample tip ejection mechanism, the sample tip ejection mechanism comprising an annular collar disposed around the sensing column, the annular collar coupled to the lever, the lever being biased by a spring and, with the lever in the first position, the lever being moveable against the spring wherein the annular collar engages the sample tip for displacing the sample tip from the sample tip retainer portion.

17. Apparatus for measuring hemostasis comprising:
   (a) sample retention apparatus comprising:
      a sample cup; and
      a sample tip received within the sample cup and defining a sample space between an inner wall of the sample cup and an outer surface of the sample tip;
   (b) sample articulation apparatus comprising:
      a drive motor having an output shaft;
      a cam coupled to the output shaft for rotation therewith in response to operation of the drive motor;
      a cam follower engaging the cam, the cam follower articulated in response to rotation of the cam;
      a drive ring coupled to the cam follower and articulated therewith; and
      at least one guide shaft extending from the drive ring;
   (c) measuring apparatus including a sensing column, the sensing column including a sample tip retainer portion; and
   (d) a sample carrier secured to and axially moveable along said guide shaft between a sample ready position, a sample test position and a sample ejection position, the sample carrier including a cavity within which the sample cup is received and a sample temperature controller wherein with the sample carrier at the sample test position, the sample tip is engaged with the sample tip retainer portion on the sensing column.

18. The apparatus of claim 17, wherein the sample temperature controller comprises a temperature sensor and a heater.

19. The apparatus of claim 17, wherein the measuring apparatus comprises an annular flange, the sample carrier comprises a planar surface, and
   with the sample carrier in the sample test position, the annular flange and the planar surface form a chamber around the sample retention apparatus.

20. The apparatus of claim 17, wherein the sample tip comprises a radially outwardly extending flange, the flange extending over and covering the sample cup.

21. The apparatus of claim 17, further comprising:
   a second cam follower engaging the cam, the second cam follower articulated in response to rotation of the cam;
   a second drive ring coupled to the second cam follower and articulated therewith; and
   at least a second guide shaft extending from the second drive ring;
   second measuring apparatus including a second sensing column; and
   a second sample carrier secured to and axially moveable along said second guide shaft between a second sample ready position, a second sample test position and a second sample ejection position, the second sample carrier including a second cavity within which a second sample cup is received and a second sample temperature controller independent of said sample temperature controller.

22. Apparatus for measuring hemostasis comprising.
   (a) sample retention apparatus comprising;
      a sample cup; and a sample tip received within the sample cup and defining a sample space between an inner wall of the sample cup and an outer surface of the sample tip;
(b) sample articulation apparatus comprising:
a drive motor having an output shaft;
a cam coupled to the output shaft for rotation therewith in response to operation of the drive motor;
a cam follower engaging the cam, the cam follower articulated in response to rotation of the cam;
a drive ring coupled to the cam follower and articulated therewith; and
at least one guide shaft extending from the drive ring;
(c) a sample carrier secured to and axially moveable along said guide shaft between a sample ready position, a sample test position and a sample ejection position, the sample carrier including a cavity within which the sample cup is received, a sample cup ejection mechanism disposed within the cavity and a sample temperature controller;
(d) torque measuring apparatus comprising:
a non-contacting rotation detector,
a torsion spring suspended from an upper portion of the torque measuring apparatus,
a torque sensing column suspended from the torsion spring, the torque sensing column comprising a sensor portion disposed adjacent the non-contacting rotation detector, a sample tip retainer portion at a lower end onto which the sample tip is received and a lock flange, and
a torque sensing column lock secured within the torque measuring apparatus, the torque sensing column lock including a lever moveable between a first position and a second position, a lock cam engaged with the lever and a release block engaged between the lock cam and a sample tip ejection mechanism coupled to the lever, wherein, with the lever in the first position, the release block is engaged with the lock flange and, with the lever in the second position, the release block is released from the lock flange.

23. A method of measuring hemostasis comprising the steps of:
providing a sample carrier axially slidable along a guide shaft with respect to a sensing apparatus;
providing a sample drive apparatus coupled to the guide shaft to drive the sample carrier in a periodic motion;
positioning the sample carrier to a sample ready position;
providing a sample retention apparatus, the sample retention apparatus comprising a sample cup and a sample tip received within the sample cup, and disposing the sample retention apparatus within the sample carrier;
positioning the sample carrier to a sample test position wherein the sample carrier is adjacent the sensing apparatus;
engaging the sample tip with the sensing apparatus;
disposing a sample within the sample cup;
disposing the sample tip in the sample; and
driving the sample carrier in the periodic motion and measuring an output at the sample tip with the sensing apparatus, wherein the output is indicative of hemostasis.

24. The method of claim 23, wherein the step of engaging the sample tip with the sensing apparatus comprises the step of engaging the sample cup with the sample tip.

25. The method of claim 23, further comprising the steps of:
ejecting the sample tip from the sensing apparatus and into the sample cup;
positioning the sample carrier to a sample ejection position; and
ejecting the sample retention apparatus from the sample carrier.

26. The method of claim 25, wherein the step of ejecting the sample tip comprises providing a sample tip ejection mechanism within the sensing apparatus.

27. The method of claim 25, wherein the step of ejecting the sample retention apparatus comprises providing a sample retention ejection mechanism within the sample carrier.

28. The method of claim 23, further comprising the step of protecting the sample.

29. The method of claim 28, wherein the step of protecting the sample comprises providing a radially outwardly extending flange formed on the sample tip, wherein the flange covers the sample cup.

30. The method of claim 28, wherein the step of protecting the sample comprises the steps of:
providing an annular flange formed on the sensing apparatus
engaging the annular flange with a surface of the sample carrier with the sample carrier in the sample test position for forming a chamber around the sample retention apparatus.

31. The method of claim 23, further comprising the step of controlling the temperature of the sample during the measurement of hemostasis.

32. The method of claim 23, further comprising the steps of:
providing an access port in the sensing apparatus, the access port being in communication with the sample retention apparatus, and
disposing a sample protecting fluid into the sample retention apparatus through the access port.

33. The method of claim 23, further comprising the step of adjusting the sensitivity of the sensing apparatus.

34. The method of claim 33, wherein the step of adjusting the sensitivity of the sensing apparatus comprises:
providing an aperture in an upper portion of the sensing apparatus;
locking a sensing column of the sensing apparatus;
decoupling the sensing column from a sensing element;
withdrawing the sensing element through the aperture;
inserting a replacement sensing element through the aperture;
coupling the sensing column to the replacement sensing element; and
unlocking the sensing column.

* * * * *